(12) United States Patent
Harper et al.

(10) Patent No.: US 8,287,811 B1
(45) Date of Patent: Oct. 16, 2012

(54) DISCREET PASSIVE EXPLOSIVE DETECTION THROUGH 2-SIDED WAVE GUIDED FLUORESCENCE

(75) Inventors: Ross James Harper, Stillwater, OK (US); Marcus la Grone, Cushing, OK (US); Mark Fisher, Stillwater, OK (US)

(73) Assignee: Flir Systems, Inc., Wilsonville, OR (US)

( * ) Notice: Subject to any disclaimer, the term of this patent is extended or adjusted under 35 U.S.C. 154(b) by 0 days.

(21) Appl. No.: 13/233,178

(22) Filed: Sep. 15, 2011

Related U.S. Application Data (62) Division of application No. 11/999,144, filed on Dec. 4, 2007, now Pat. No. 8,038,946.

(60) Provisional application No. 60/872,940, filed on Dec. 4, 2006.

(51) Int. Cl.
| | |
|---|---|
| *G01N 21/64* | (2006.01) |
| *G01N 21/66* | (2006.01) |
| *G01N 21/00* | (2006.01) |
| *G01N 21/75* | (2006.01) |
| *G01N 21/76* | (2006.01) |

(52) U.S. Cl. .............. 422/82.07; 422/82.08; 422/82.11; 436/164; 436/172

(58) Field of Classification Search .............. 422/82.07; 436/164
See application file for complete search history.

(56) References Cited

U.S. PATENT DOCUMENTS

| | | | | |
|---|---|---|---|---|
| 6,558,626 | B1 * | 5/2003 | Aker et al. ............. | 422/91 |
| 7,002,681 | B1 * | 2/2006 | Arrieta et al. ............. | 356/317 |
| 8,038,946 | B1 * | 10/2011 | Harper et al. ............. | 422/82.07 |

* cited by examiner

*Primary Examiner* — Sam P Siefke
*Assistant Examiner* — Bryan Kilpatrick
(74) *Attorney, Agent, or Firm* — McAfee & Taft (57) ABSTRACT

The current invention provides a passive sampling device suitable for collecting and detecting the presence of target analytes. In particular, the passive sampling device is suitable for detecting nitro-aromatic compounds. The current invention further provides a passive sampling device reader suitable for determining the collection of target analytes. Additionally, the current invention provides methods for detecting target analytes using the passive sampling device and the passive sampling device reader.

16 Claims, 12 Drawing Sheets

DISCREET PASSIVE EXPLOSIVE DETECTION THROUGH 2-SIDED WAVE GUIDED FLUORESCENCE

CROSS REFERENCE TO RELATED APPLICATION

This application claims priority from U.S. Provisional Patent Application Ser. No. 60/872,940 filed on Dec. 4, 2006, the entire contents of which are incorporated herein by reference. Additionally, this application is a divisional of U.S. Ser. No. 11/999,144, filed on Dec. 4, 2007 now U.S. Pat. No. 8,038,946.

GOVERNMENT RIGHTS STATEMENT

This invention was developed in part with support by the United States Department of Energy (DOE) through Order No. 532539 issued by Sandia Corporation, operator of Sandia National Laboratories under Contract Number DE-AC04-94AL85000 for the DOE. The United States Government may have rights in and to this application by virtue of this funding.

BACKGROUND OF THE INVENTION

The current invention is related to improved passive sampling devices, sampling device readers and methods for detecting explosives in the environment.

Real-time, active detection devices such as described in U.S. Pat. No. 6,558,626 are now used as checkpoint devices to monitor vehicles for explosives. These devices require active involvement of the user to monitor the device for positive results and for maintenance purposes. While the value of the active detection devices has been repeatedly demonstrated, they are of limited use for long term passive monitoring of storage facilities and other low traffic areas.

Therefore, it would be beneficial to provide passive sampling devices which do not require human involvement to monitor for the presence of explosive compounds. Such passive devices would preferably have the ability to capture and retain traces of such compounds over long periods of time. Additionally, the passive sampling device should be easily interrogated to yield a positive or negative result for the presence of explosives. Preferably, the passive sampling device would be scanned by a reader which automatically indicates a positive or negative result for explosives.

SUMMARY OF THE INVENTION

In one embodiment, the current invention provides a passive sampling device suitable for monitoring an area for the presence of a target analyte. The passive sampling device of the present invention is particularly suitable for monitoring an area for the presence of nitro-aromatic compounds. In a preferred embodiment, the passive sampling device comprises a waveguide having first and second sides. On one side, the waveguide carries at least one amplifying fluorescent polymer (AFP). The AFP fluoresces when stimulated with UV light or near UV light. On the other side, the waveguide carries a reference standard which fluoresces at a wavelength distinct from the AFP when stimulated with the same UV/near UV light. The AFP is selected for its ability to capture and retain traces of the target analyte. When the AFP has captured the target analyte the fluorescence resulting from excitement with the UV/near UV light source will be quenched.

In another embodiment, the current invention provides a passive sampling device reader. The passive sampling device reader comprises a UV/near UV light source, a holder or port for receiving and holding the passive sampling device, a series of filters selected to correspond to the fluorescence wavelength of the AFP, the reference standard and a preferred baseline. Additionally, the passive sampling device comprises a photo multiplier tube suitable for reading the intensity of fluorescence by the AFP and the reference standard. The fluorescence intensity or a value representing whether or not a positive test for analytes has occurred is depicted on a LCD or other similar display.

In another embodiment, the current invention provides a method for determining the presence of target analytes. In the method of the current invention, a passive sampling device is prepared using an AFP selected for its ability to capture and retain the target analyte as well as the ability to fluoresce when exposed to UV/near UV light. The passive sampling device is also provided with a reference standard. Following preparation of the passive sampling device, the passive sampling device is exposed to UV/near UV light to determine the fluorescence intensity of the AFP and reference standard prior to exposure to the target analyte. Subsequently, the passive sampling device is placed in a test area for a period of time. Upon collection of passive sampling device from the test area the passive sampling device is exposed to UV/near UV light to determine the fluorescence intensity of the AFP and reference standard. A reduction in fluorescence value for the AFP without a corresponding reduction in fluorescence value for the reference standard indicates a positive result for exposure to the target analyte.

DETAILED DESCRIPTION OF THE INVENTION

The current invention provides a method for detecting nitroaromatic compounds. The method of the current invention utilizes a passive sampling device (PSD) and a passive sampling device reader (PSDR). As used herein, the term passive sampling device refers to a device which does not require the active movement of air in order to detect a target analyte. Thus, the current invention does not rely on pumps or other similar air movement devices.

A non-limiting list of compounds detectible by the PSD described herein includes 2,4,6-Trinitrotoluene (TNT); 1,3,5-Trinitrobenzene (TNB); 2,4,6-Trinitro-m-xylene (TNX); 2,4,6-Trinitrochlorobenzene (picryl chloride); 2,4,6-Trinitrophenol (picric acid); ammonium picrate (Explosive D); 2,4,6-Trinitro-m-cresol (TNC); 2,4,6-Trinitroresorcinol (styphnic acid); 2,4,6-Trinitroanisole (TNA, methyl picrate); 2,4,6-Trinitrophenetole (TNP, ethyl picrate); 2,4,6-Trinitroaniline (picramide, 1-monoamino-2,4,6-trinitrobenzene, MATB); 1,3-Diamino-2,4,6-trinitrobenzene (DATB); 1,3,5-Triamino-2,4,6-trinitrobenzene (TATB); and 2,4,6,N-Tetranitro-N-methylaniline (tetryl, 2,4,6-trinitrophenylmethylnitramine). Other substances that may be detected by the present invention include, but are not limited to, 2-amino-4,6-dinitrotoluene, 4-amino-2,6-dinitrotoluene, 2-amino-4-nitrotoluene, 3,5-dinitroaniline, 1,3-dinitrobenzene, 2,4-dinitrotoluene, 3-nitroaniline, and 2,4,6-trinitroaniline.

Passive Sampling Device for Detecting Nitroaromatic Compounds

The sampling device of the current invention takes advantage of known responses to ultraviolet light and near UV light by a class of organic compounds known as amplifying fluorescent polymers (AFP). As used in the remainder of this specification, the terms UV light, UV excitation source and UV light source refer to wavelengths between about 365 nm and 410 nm and devices for producing light in this range, i.e. UV to near UV light. These compounds are described in U.S. Pat. No. 7,208,122, filed on Dec. 18, 2002, entitled "Emissive Polymers and Devices Incorporating These Polymers," originally filed as U.S. Ser. No. 60/084,247, on May 5, 1998. The entire contents of the provisional application and U.S. Pat. No. 7,208,122 are incorporated herein by reference. As discussed in the '122 patent, due to the luminescent and conductive properties of AFP these compounds are particularly suited for sensing analytes such as nitro-aromatic compounds.

Traditional fluorescence detection schemes measure a change in fluorescence intensity when a molecule of analyte interacts with a single fluorescent probe molecule. In prior art methods, a photon of light must be absorbed by the fluorescent probe molecule while a molecule of analyte is interacting with the probe molecule. When the analyte molecule interacts with the fluorescent probe molecule, either an increase or decrease in the intensity of fluorescence is observed.

The AFP compounds have conjugated polymer backbone extending the length of the polymer chain. When stimulated by UV light, the polymer absorbs a single photon of light which produces an exciton (an excited-state electron) that migrates along the polymer backbone and also between polymer chains in solid phase films of the polymer. If the exciton is free to travel the polymer, fluorescence will occur. Along this polymer backbone, the AFP compound carries a plurality of receptor sites. If the exciton encounters an analyte molecule bound to one of many receptor sites on the polymer molecule as it migrates through the polymer, the exciton will be trapped precluding fluorescence from the photon absorption event. This process is referred to as fluorescence quenching. Thus, the quenching of AFP fluorescence can be used to determine exposure of the AFP to a target analyte.

In contrast to AFP, traditional fluorescence sensing schemes confine the excited state electron to the absorbing fluorescent probe molecule, thereby "sampling" only one "receptor site." In AFP, the exciton can sample many receptor sites, thereby significantly increasing the number of receptor sites sampled per photon absorbed when compared to a monomeric chromophoric system thereby increasing sensitivity of the polymer to the target analytes. In addition, the receptor sites on AFP are carefully designed and synthesized to preferentially bind to only certain types of molecules. Thus, a properly formulated AFP compound preferentially captures and retains a narrow class of chemical compounds, rather than responding to many chemical analytes.

The current invention utilizes AFP compounds in a PSD 5 suitable for detecting nitroaromatic compounds. Passive sampling device 5 comprises a waveguide 10 capable of transmitting UV light. In the preferred embodiment, both sides 14, 18 of waveguide 10 are coated with fluorescent materials. First side 14 is coated with AFP, identified in FIG. 1 with the number 22. Second side 18 carries a suitable reference standard, identified in FIG. 1 with the number 24. In a preferred embodiment, waveguide 10 is a transparent glass cover slip of the type commonly used with microscopes. In the preferred embodiment, UV light with wavelengths between about 365 nm and 410 nm will excite AFP compound 22 and reference standard 24 generating a photon, i.e. an exciton.

As noted above, the AFP compounds described in U.S. Pat. No. 7,208,122 are suitable for use in the current invention. As other AFP compounds are created they will also likely be suitable for use in the current invention. The compounds depicted in FIGS. 10a through 10e are representative of compounds useful as AFP 22. The presently preferred compound for use as AFP 22 is AFP Polymer-1 depicted in FIG. 10a.

Figure 10A:
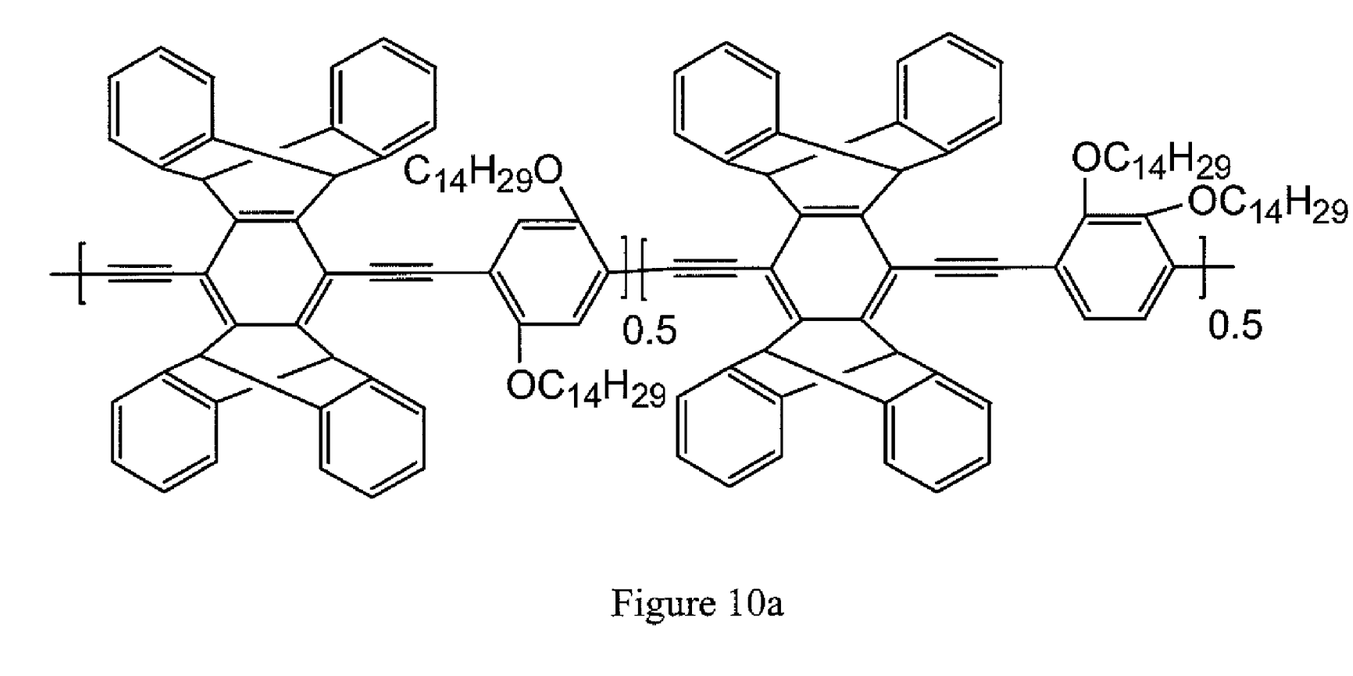
FIGS. 10a, 10b, 10c, 10d and 10e are representative compounds suitable for use on passive sampling device as analyte capturing compounds.
Figure 10B:
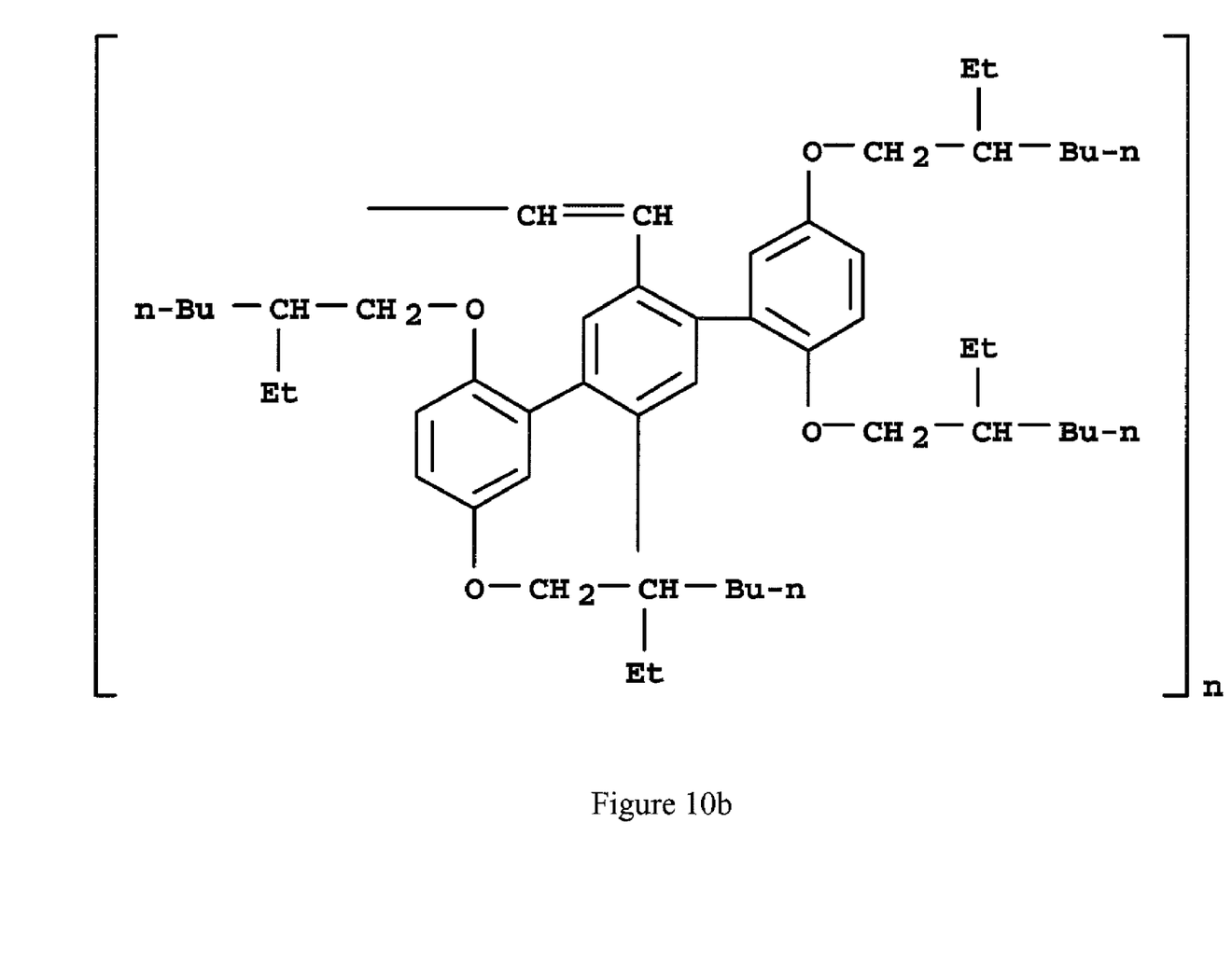
Figure 10C:
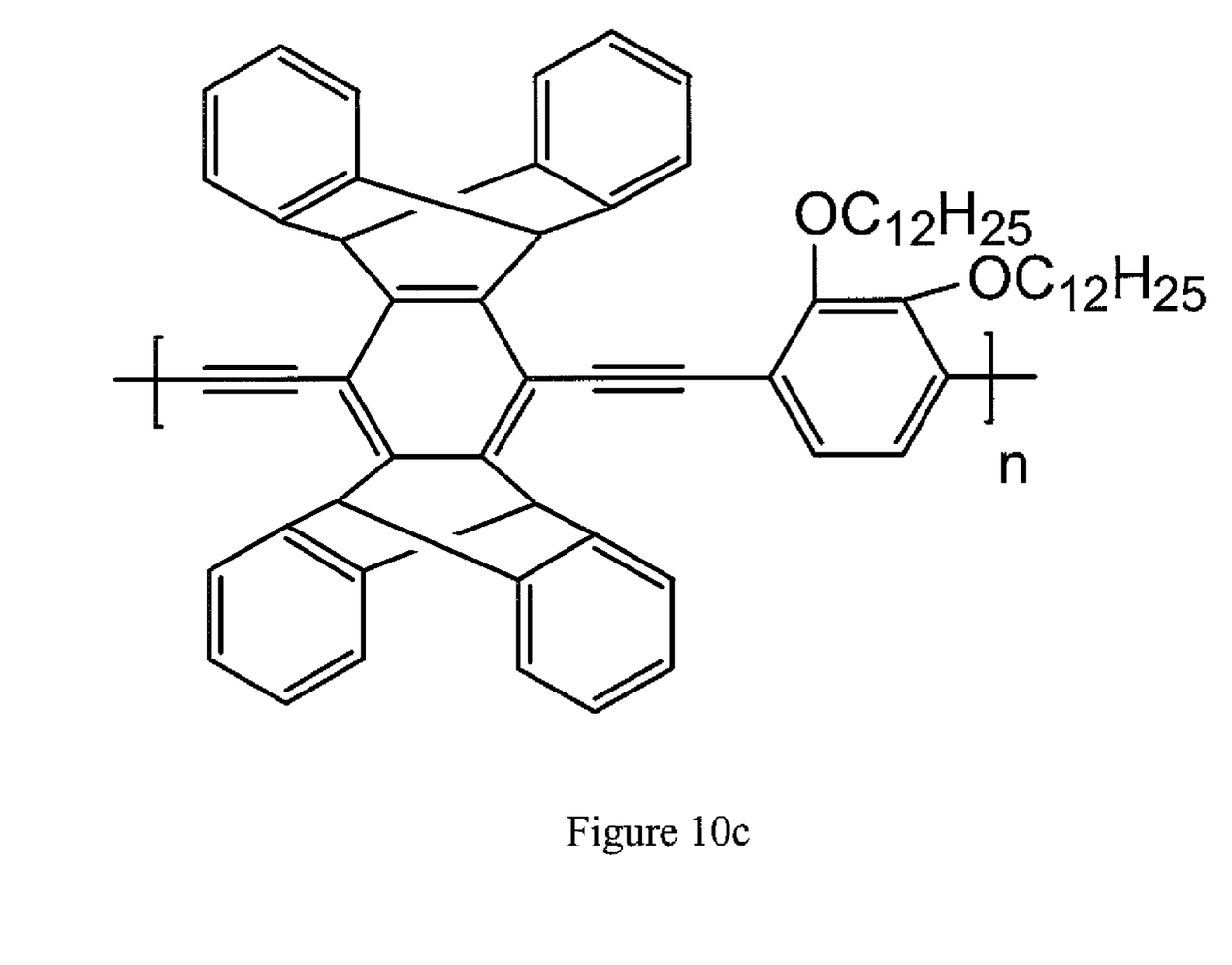
Figure 10D:
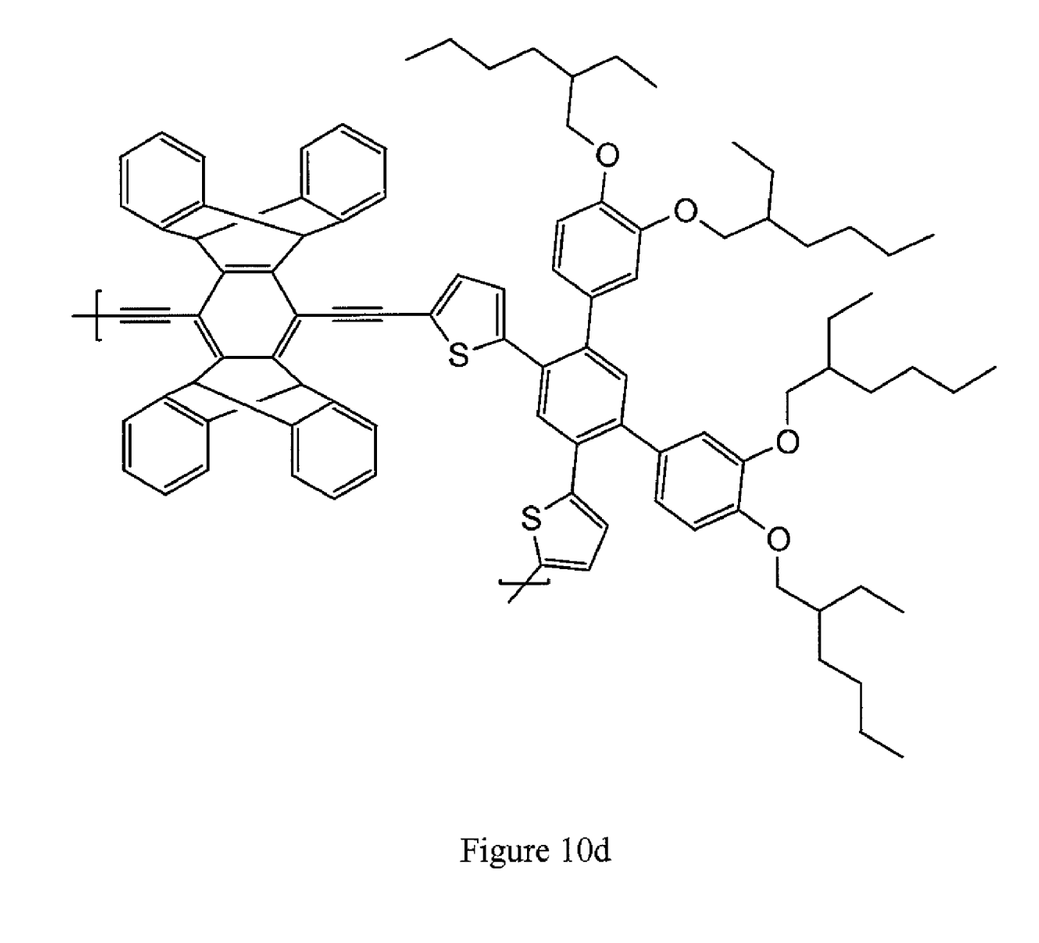
Figure 10E:
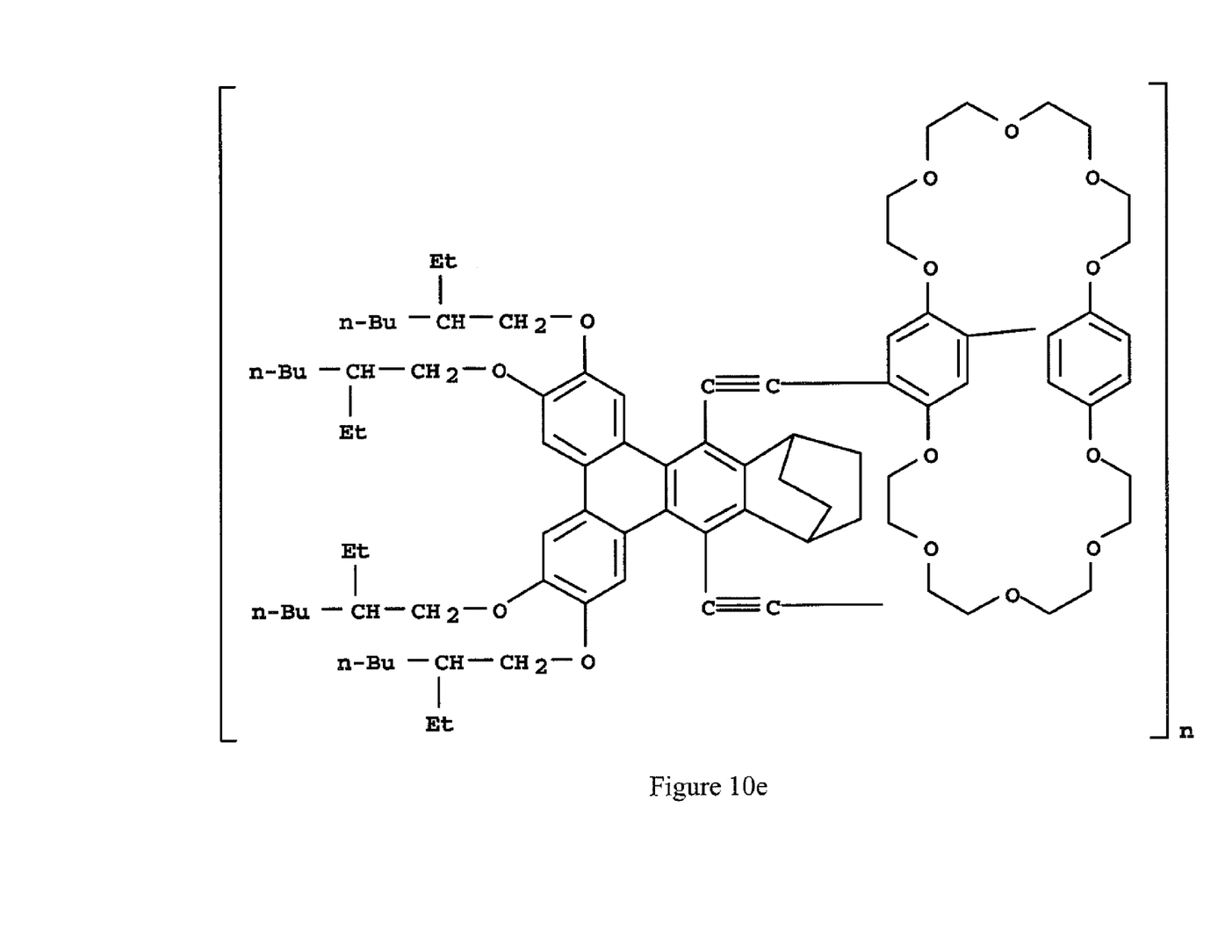

Polymer-1 has the chemical formula $(C_{72}H_{80}O_2)n$ and is known as poly[(5,7,12,14-tetrahydro-5,14[1',2']:7,12-[1",2"]-dibenzenopentacene-6,13-diyl)-1,2-ethynediyl[2,5-bis(tetradecyloxy)-1,4-phenylene]-1,2-ethynediyl]. Polymer-1 has been assigned Chemical Abstracts Registry No. 220081-22-1. FIG. 10b, also known as Polymer-2, has the chemical formula $(C_{52}H_{78}O_4)n$ and the chemical name poly[[2,2",5,5"-tetrakis[(2-ethylhexyl)oxy][1,1':4',1"-terphenyl]-2',5'-diyl]-1,2-ethenediyl]. Polymer-2 as been assigned Registry No. 853053-63-1. AFP Polymer-3, depicted as FIG. 10c, has the chemical formula of $(C_{68}H_{72}O_2)n$ and the chemical name poly[(5,7,12,14-tetrahydro-5,14[1',2']:7,12[1",2"]-dibenzenopentacene-6,13-diyl)-1,2-ethynediyl[2,3-bis(dodecyloxy)-1,4-phenylene]-1,2-ethynediyl]. Polymer-3 has been assigned Registry No. 386285-10-5. AFP Polymer-4 is depicted in FIG. 10d. Polymer-4 has been assigned Registry No. 444922-16-1 and has the chemical formula of $(C_{96}H_{100}O_4S_2)n$. Polymer-4 has the chemical name of poly[2,5-thiophenediyl[3,3",4,4"-tetrakis[(2-ethylhexyl)oxy][1,1':3',1"-terphenyl]-4',6'-diyl]-2,5-thiophenediyl-1,2-ethynediyl(5,7,12,14-tetrahydro-5,14[1'2']:7,12[1",2"]-dibenzenopentacene-6,13-diyl)-1,2-ethynediyl]. AFP Polymer-5 is depicted in FIG. 10e. Polymer-5 has been assigned Registry No. 383429-38-7 and has the chemical formula of $(C_{88}H_{120}O_{14})n$. Polymer-4 has the chemical name of poly[2,5,8,11,14,19,22,25,28,31-decaoxatricyclo[30.2.2.215,18]octatriaconta-15,17,32,34,35,37-hexaene-16,37-diyl-1,2-ethynediyl[2,3,6,7-tetrakis[(2-ethylhexyl)oxy]-10,11,12,13-tetrahydro-10,13-ethanobenzo[b]triphenylene-9,14-diyl]-1,2-ethynediyl].

Figure 1:
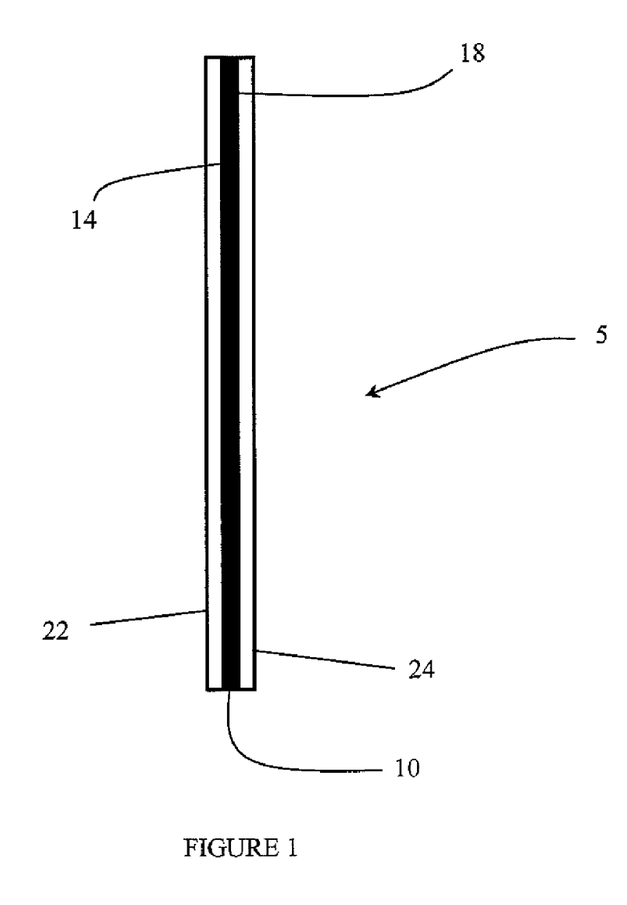
FIG. 1 is a depiction of the edge of a preferred sampling device of the current invention showing the layers of fluorescent materials.

The preferred embodiment is selected to isolate AFP 22 from reference standard 24 thereby precluding the occurrence of Fluorescent Resonance Energy Transfer (FRET). Thus, the separation of the AFP from the reference standard enhances the reliability and accuracy of the sampling device when read by a suitable fluorometer. Additionally, the preferred configuration of PSD 5 permits interrogation with a single UV excitation source 40, also referred to as UV light source 40, as both sides 14, 18 are excited simultaneously. Further, discussion concerning interrogation of PSD 5 is provided below.

Figure 9:
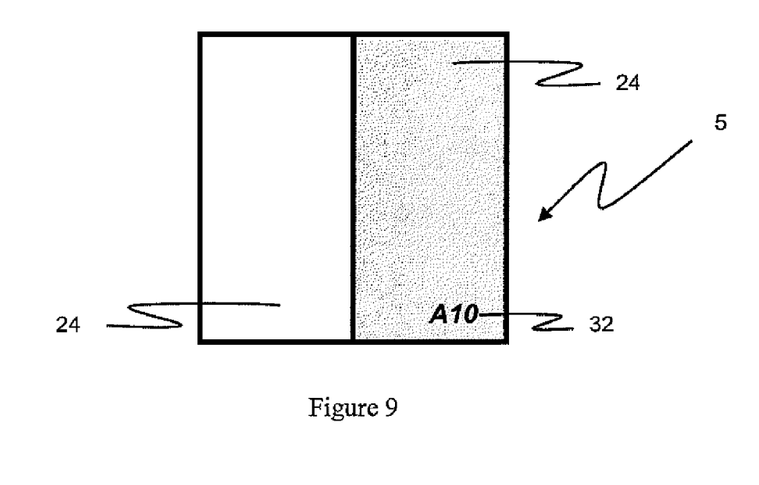
FIG. 9 depicts a passive sampling device with amplifying fluorescent polymer and reference standard on a single side.

However, other similar transparent materials or waveguides may be substituted without degradation in performance. For example, as shown in FIG. 9, a single sided PSD may be used provided that AFP 22 and reference standard 24 are not commingled. Separation of AFP 22 and reference standard may be provided by a physical barrier or through the application technique. In this alternative embodiment, FRET does not occur due to the isolation of the two components. The following discussion will focus on the preferred embodiment; however, one skilled in the art will readily recognize the functionality of a single sided PSD 5 from the teachings provided herein.

Typically, AFP coating 22 applied to side 14 will have a thickness ranging from about 100 angstroms to about 1 micron. If a particular target analyte is of interest, then the thickness of AFP coating 22 will be adjusted to a range selected to improve capture and retention of the target analyte. For example, a thicker coating is preferred when the target analyte is dinitrotoluene (DNT) and other generally more volatile nitro-aromatic compounds while a thinner coat would be appropriate for less volatile compounds such as TNT. A preferred AFP coating 22 for capture and retention of DNT and similar compounds would have a thickness in the range of about 10 to 100 nanometers. When the target analyte is TNT and similar compounds, the preferred thickness for AFP coating 22 is in the range of about 1 to 10 nanometers.

Figure 6:
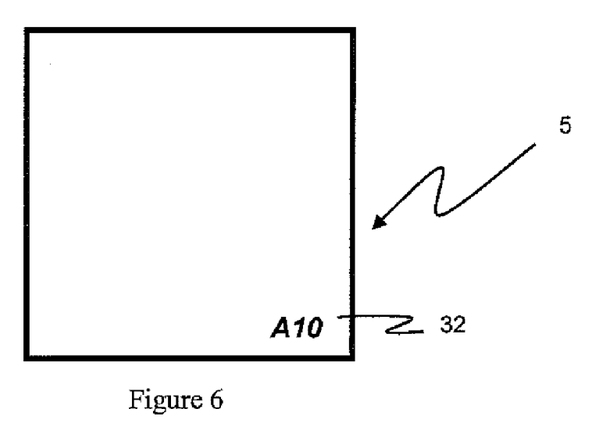
FIG. 6 is a top view of a preferred embodiment of a passive sampling device.
Figure 7:
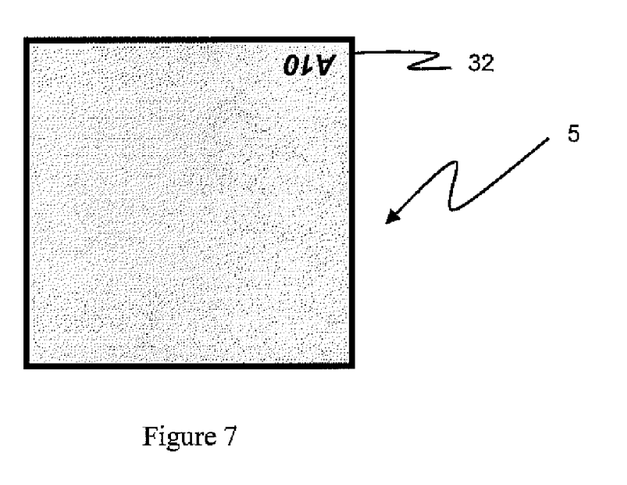
FIG. 7 is a bottom view of a preferred embodiment of a passive sampling device.

In a preferred embodiment, side 14 is completely coated with AFP 22 and side 18 is completely coated with the reference standard 24. However, completely coating entire sides 14 and 18 is not a requirement for operability of the current invention. Rather, the area covered by AFP 22 and reference standard 24 must be sufficient to permit interrogation by the Passive Sampling Device Reader 28. Typically, to ensure proper orientation during interrogation by PSDR 28, each side 14, 18 carries an identifying mark 32 in one corner of each side 14, 18 of PSD 5. Each mark 32 is selected to identify either side 14 or 18. While each side 14, 18 preferably carries identifying mark 32, the mark is optional or may be optionally carried by only one side.

Figure 8:
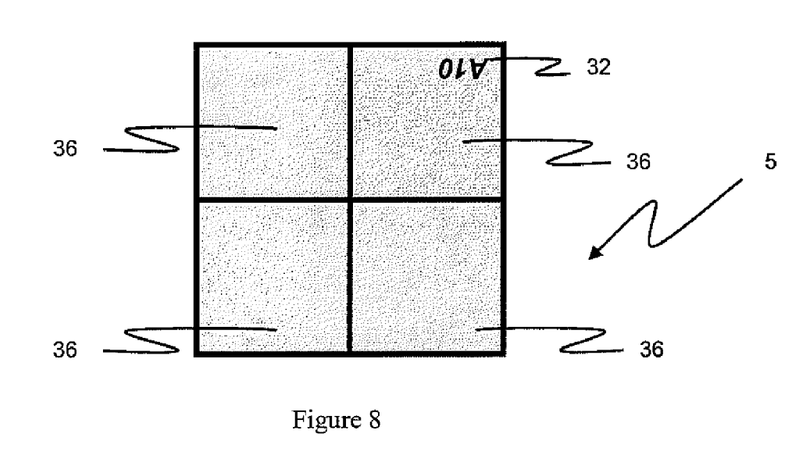
FIG. 8 depicts a top view of an alternative embodiment of passive sampling device having a plurality of sampling zones.

As depicted in FIG. 8, an alternative embodiment of PSD 5 comprises a plurality of sensing zones 36 on side 14. Each sensing zone 36 consists of either a different AFP 22 or a different thickness of AFP 22. The ability to provide a plurality of sensing zones 36 enhances the accuracy and flexibility of PSD 5. In one embodiment comprising a plurality of sensing zones 36, PSD 5 provides for detection of a plurality of analytes by utilizing different AFP compounds, different thicknesses of the same AFP compound or a combination thereof.

Use of a plurality of sensing zones 36 minimizes the number of false positives. In this embodiment, the ratio of pre-exposure versus post exposure fluorescence is known for a given analyte for each sensing zone 36. Following collection of PSD 5 and interrogation by PSDR 28, a positive response for each sensing zone 36 with the correct quench ratio indicates presence of the target analyte. In contrast, a positive response for only one sensing zone 36, is likely a false positive. A detailed discussion of the interrogation method is provided below.

In each of the foregoing embodiments, AFP compounds 22 and reference compound 24 are applied to waveguide 10 by any convenient means suitable for providing a uniform coat of the desired thickness. Spin coating is one suitable method for applying the compounds. Alternatively, inkjet printing is used to apply both AFP 22 and reference standard 24 to waveguide 10. Inkjet printing is particularly suitable for providing multiple sensing zones 36 on a single waveguide 10. In an alternative embodiment, an inkjet printer can be used to apply AFP 22 in a predetermined pattern thereby permitting pattern identification when waveguide 10 is interrogated by UV light source 40.

The size of PSD 5 may be varied as desired. When PSD 5 carries a single sensing zone 36, PSD 5 is generally square in shape. In this configuration a standard 18 mm cover slide having a thickness of about 0.25 mm is a suitable waveguide 10 for carrying AFP 22 and reference standard 24. When a plurality of sensing zones 36 are desired, the configuration of PSD 5 may be altered as necessary to accommodate the desired number of zones 36.

This flexibility in the configuration of PSD 5 permits application and sampling in a wide variety of areas. For example, PSD 5 may be configured for inclusion in identity/security badges (not shown) to serve as dosimeters for exposure to explosive compounds. Additionally, single and multi-zone PSD 5 may be configured for use within heating and ventilation systems to serve as a long term monitor. Thus, the width, length and thickness as well as the configuration of PSD 5 is readily adaptable for a variety of applications. In general, the only limitation on size of PSD 5 is the ability to act as a suitable waveguide and practical ability for use in the field.

As noted above, first side 14 of waveguide 10 is coated with AFP 22. The preferred AFP is extremely sensitive to the nitroaromatic target materials, such as TNT, explosives. Prior to exposure to the target analyte, the preferred AFP will fluoresce when excited with UV to near UV light (365-410 nm). During fluorescence, AFP emits light in the blue spectrum with a wavelength between about 450 to about 480 nm. Generally, the preferred AFP compound will fluoresce at a wavelength of about 465 nm. When the AFP comes into contact with a nitro-aromatic compound the fluorescence is reduced in a process referred to as quenching. This reduction is exponential due to the structure of the polymer backbone leading to enhanced sensitivity.

Side 18 of waveguide 10 is coated with suitable reference standard 24. For example, a preferred reference standard 24 is a permanent fluorescent dye which excites in a similar near-UV range, but emits light at a much longer wavelength in the red range, requiring a large Stokes shift. Alternatively, PSD 5 may incorporate a blend of dyes as reference standard 24. As with the use of a single dye, the blend of dyes is selected to produce detectible light at wavelength different from AFP22. Use of a blend of dyes will compensate for circumstances where a single dye does not produce a sufficient Stokes shift. The multiple dyes will provide a stepwise alternative where FRET results in the emission of the first dye being absorbed by the next dye until a detectible emission of light is produced.

In the preferred embodiment, reference standard 24 will fluoresce at a wavelength of at least 580 nm. Preferably, reference standard 24 will fluoresce at about 620 nm. Preferably, the target analyte does not alter the fluorescence of the preferred permanent fluorescent dye. For example, exposure of PSD 5 to nitro-aromatic compounds will quench only the fluorescence of AFP compound 22 while the fluorescence of reference standard 24 is substantially unchanged by exposure to the target analyte. More preferably, the fluorescent emission of reference standard 24 is unchanged by exposure to nitro-aromatic compounds and any other target analyte.

Single dyes with sufficient Stokes shift suitable for use as reference standard 24 include but are not limited to: tetrakis-(4-carboxyphenyl) porphines, tetrakis-(4-sulphophenyl) porphines, ruby, ethidium bromide, texas red or rubrene, and it derivatives, phenyl and phenylethynel chlorinated polycyclic aromatic hydrocarbons such as perylene, tetracene, and pentacene and derivatives thereof. The preferred dye is ruby. Additionally, the preferred thickness of reference standard 24 is from about 100 angstroms to about 1 micron.

In contrast to active detection devices, PSD 5 does not require a quick recovery time following quenching of AFP 22. Rather, AFP 22 is selected and applied in a thickness to enhance retention of the target analyte, thereby prolonging the quenching of fluorescence. Thus, PSD 5 provides for long term passive collection and subsequent analysis for the target analyte either at the test site or in a lab. As will be discussed in detail below, any exposure of PSD 5 to the target analyte will result in capture and retention of the analyte by AFP 22 leading to a positive test when interrogated by PSDR 28. In general, the current invention provides the ability to detect nitro-aromatic compounds at concentrations of less than 1 part per billion.

Method and Device for Reading the PSD

As noted above, PSD 5 is interrogated by PSDR 28 to determine the presence of the target analyte. A preferred PSDR 28 is a fluorometer. Fluorometers are also sometimes referred to as luminescence spectrometers, fluorimeters, fluorescence spectrometers or spectrofluorometers.

Fluorometers measure the amount of fluorescent radiation produced by a sample exposed to monochromatic radiation. They contain filters for excitation and emission but no wavelength scanning. Light is collected at 90 degrees from the incident light (excitation) direction. As known to those skilled in the art, fluorescence is a very reliable and accurate means for quantifying and detecting a compound or substance. It is a phenomenon in which light energy is absorbed by a molecule and then re-emitted again as a photon of light with a slightly longer wavelength. The phenomenon is common among organic molecules including groups of strongly fluorescent dyes, such as fluorescein (absorbs blue, emits yellow-green light), the rhodamines (absorb green light, emit orange-red), and the family of stilbene optical brighteners, which absorb U/V light and emit blue.

The important parameters measured by fluorometers are the spectral or wavelength range and the accuracy and resolution of that reading. Common detector configurations of fluorometers include photomultiplier tubes and photodiodes. A photomultiplier tube is a photo-detector, with adjustable voltage, that translates optical tube signals into electrical current. Increasing the photo multiplier tube voltage increases the output signal for a given amount of light. A photodiode is a semiconductor device used to detect light and generate an electrical current. Photodiode detectors are typically used in forward scatter (FSC) detection. Common features for fluorometers include shutters, microscope, automatic temperature compensation ability, temperature measurement ability, programmability, self-calibration and alarms.

Figure 4:
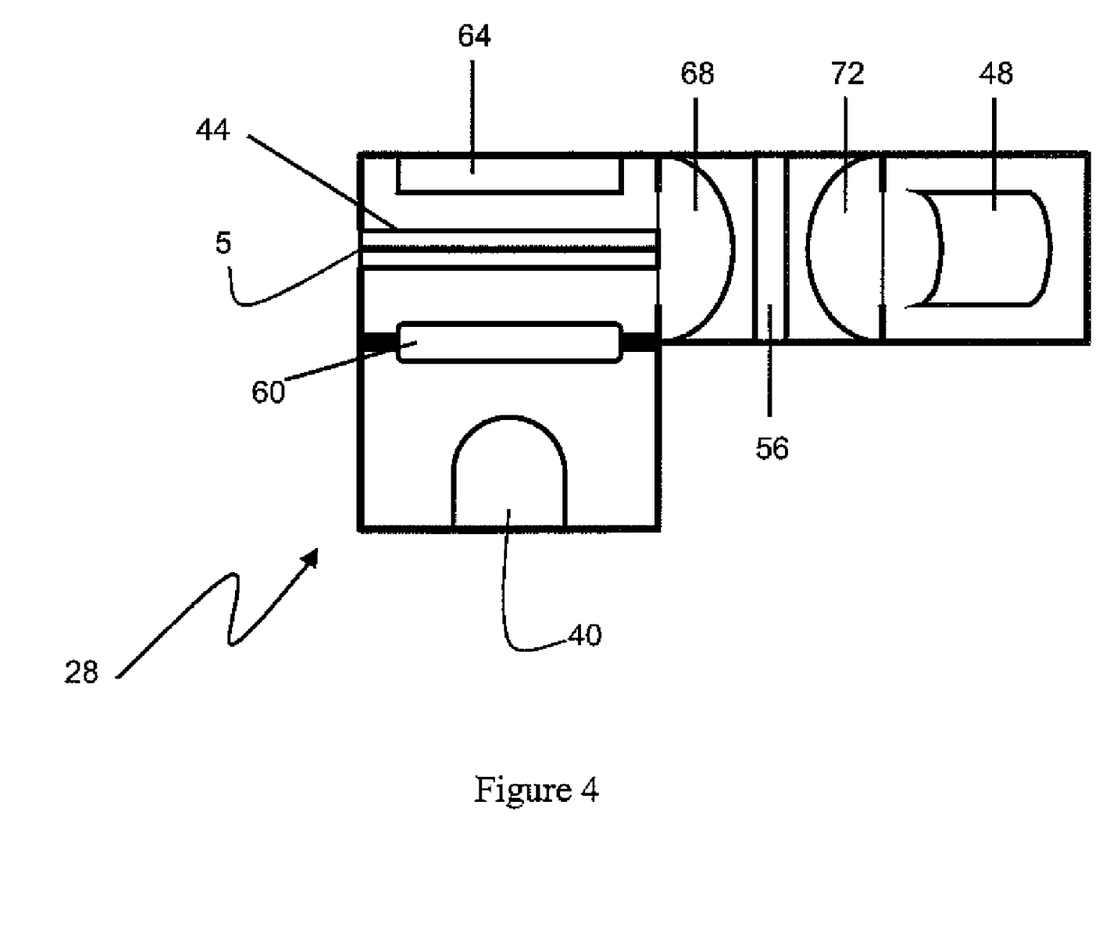
FIG. 4 is a schematic view of a passive sampling device reader suitable for interrogating a passive sampling device.
Figure 5:
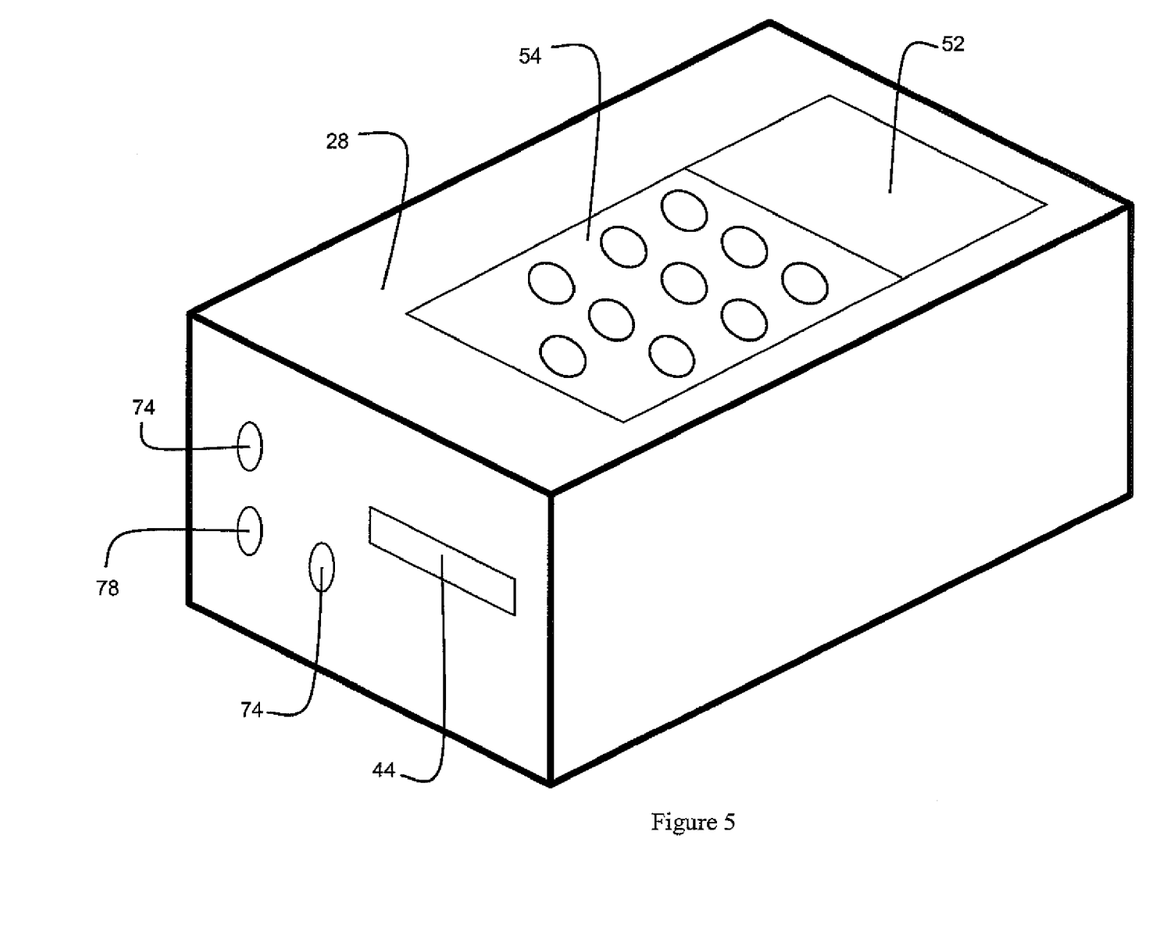
FIG. 5 is a perspective view of a passive sampling device reader.

With reference to FIGS. 4 and 5, in the preferred embodiment, PSDR 28 includes an UV excitation source 40, a PSD holder 44 sized to accept and hold PSD 5, a series of three automatically controlled short-pass filters (not shown) carried by a wheel 56 or other suitable support device, and a photo multiplier tube (PMT) 48. As shown in FIG. 4, UV excitation source 40 is a light emitting diode. However, any suitable UV source capable of emitting UV light will suffice. In the preferred embodiment, a 410 nm band pass filter 60 is placed between UV source 40 and PSD 5. Use of 410 nm band pass filter 60 precludes photons with wavelengths greater than 410 nm which may interfere with emissions produced by AFP 22. A mirror 64 located behind PSD 5 ensures maximum fluorescence of AFP 22 and reference standard 24. Resulting fluorescent light is transmitted by waveguide 10 towards PMT 48. Lenses 68, 72 focus the fluorescent light from waveguide 10 on PMT 48. In the preferred embodiment, the gain of PMT 48 is adjustable by a suitable switch 74. PSDR 28 also includes an on/off switch 76 and a power source 78 in the form of a battery or power cable.

PSDR 28 preferably includes an LCD readout screen 52 capable of providing test results in graphic display and/or numeric values and a data entry keypad 54. Optionally, PSDR 28 may be integrated with a PC or laptop computer (not shown) suitable for generating graphs and other readouts as well as storing data associated with each PSD 5 interrogated by PSDR 28.

During interrogation of PSD 5, PSD 5 is positioned within PSD holder 44 and light from UV source 40 in PSDR 28 is directed at PSD 5. Preferably, UV light (365-410 nm) simultaneously excites AFP 22 and reference standard 24 carried by PSD 5. Thus, the current invention eliminates the need to remove PSD 5 from holder 44 in order to interrogate both AFP 22 and reference standard 24. Although the light may impact PSD 5 from either side, in the examples provided below the UV light first contacted side 14 carrying AFP 22. Upon exposure to the UV light, AFP 22 and reference standard 24 will fluoresce producing a detectible fluorescent emission. The resulting fluorescent light is transferred by waveguide 10 perpendicular to the axis of the excitation source 40. Thus, waveguide 10 directs the light towards the filter wheel 56 carrying the three short-pass filters.

In the preferred embodiment, PSDR 28 automatically directs movement of wheel 56 to cycle through the filters thereby measuring the fluorescence at each selected wavelength. The resulting fluorescent light is received by PMT 48 and a readout generated and displayed on LCD screen 52. The resulting data may be depicted numerically or graphically. Graphs may be traces, bar graphs or other suitable display.

Exposure of AFP 22 to a target analyte such as a nitro-aromatic compound will reduce or quench the fluorescence of AFP exposed to UV light. The reduction in fluorescence can be measured and detected using a standard fluorometer as described above. In order to properly measure the magnitude of the quenching effect, a pre-exposure reading must be taken to establish the initial fluorescence values for each desired wavelength.

In the current invention, fluorescence values are taken at three discrete wavelengths corresponding to fluorescence values for AFP 22, reference standard 24 and a baseline fluorescence for PSD 5 at a wavelength between the peak fluorescence wavelengths for AFP 22 and reference standard 24. The baseline fluorescence value provides a reference which accommodates changes in environmental conditions. Thus, peak measurements for AFP 22 and reference standard 24 are measured against the baseline value at each interrogation of PSD 5. Any change in the environment such as temperature shifts which may impact the peak values will also likely impact the baseline value thereby providing the means to consistently interrogated PSD 5.

Thus, in the practice of the current invention, readings are observed for at least three wavelengths. Preferably, AFP fluorescence is observed at a wavelength between about 450 nm to about 480 nm. When determining exposure to nitro-aromatic compounds, the preferred wavelength will be determined by the AFP chosen for use on PSD 5. For example, when using Poly[(5,7,12,14-tetrahydro-5,14[1',2']:7,12[1'',2'']-dibenzenopentacene-6,13-diyl)-1,2-ethynediyl[2,5-bis(tetradecyloxy)-1,4-phenylene]-1,2-ethynediyl] as AFP 22, the filter will be selected to measure fluorescence at a wavelength of 460 nm. Likewise the fluorescence wavelength of reference standard 24 will vary depending on the composition of reference standard 24. In general, fluorescence for the reference standard compound is observed at a wavelength which does not interfere with AFP fluorescence. Thus, fluorescence wavelength of reference standard 24 is preferably at least 580 nm. Preferably, the reference standard is observed at 620 nm. As an example, when using preferred reference standard ruby, fluorescence is observed at 620 nm. Finally, the baseline reading or noise reading for PSD 5 is generally measured at a wavelength between about 500 nm and 580 nm. Preferably the baseline reading is measured at wavelength of about 550 nm. Thus, the three short-pass filters are selected to transmit light at the desired wavelengths for each necessary measurement. As noted above, in the preferred embodiment of PSDR 28, wheel 56 automatically positions each filter between PSD 5 and PMT 48 during interrogation of PSD 5. Alternatively, the filters may be manually changed.

Figure 2:
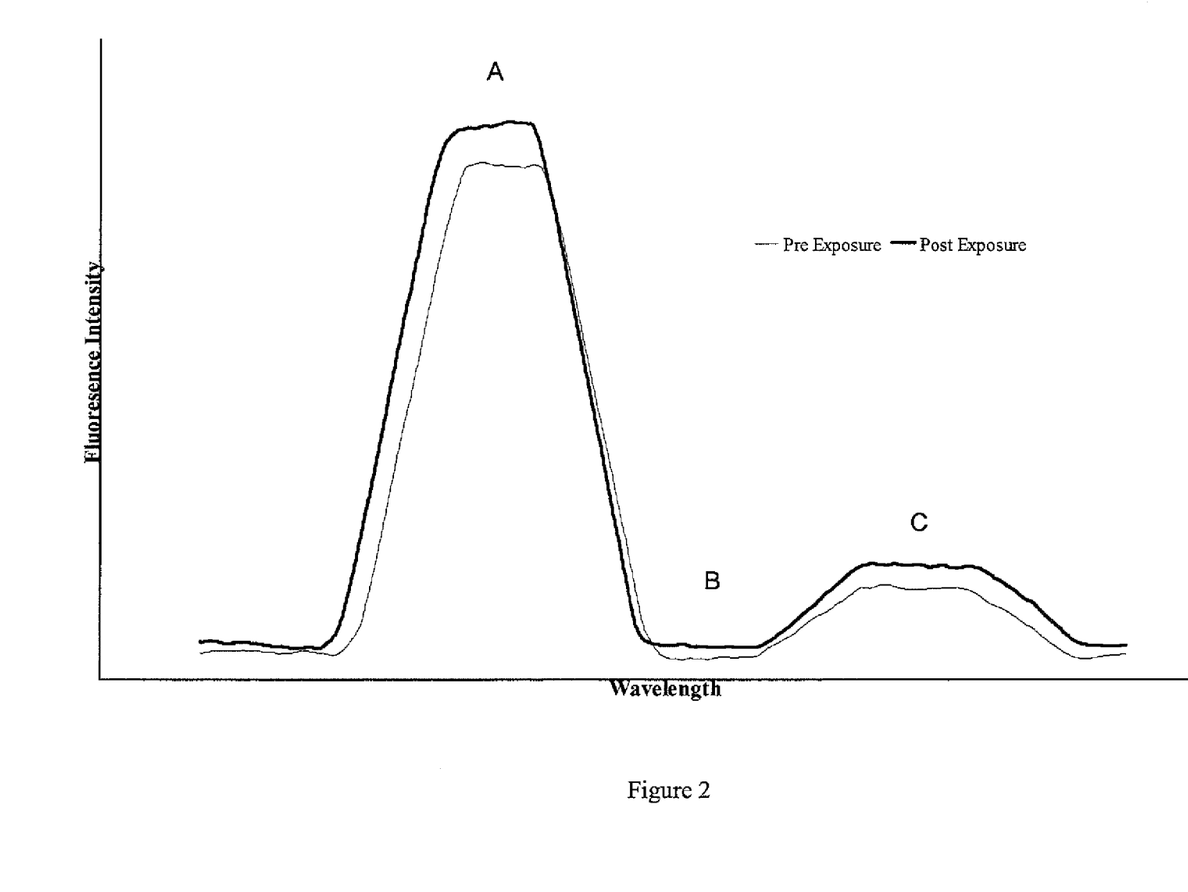
FIG. 2 is a graph depicting the display of the fluorescence values for a blank when read by a fluorometer using the method of the current invention.
Figure 3:
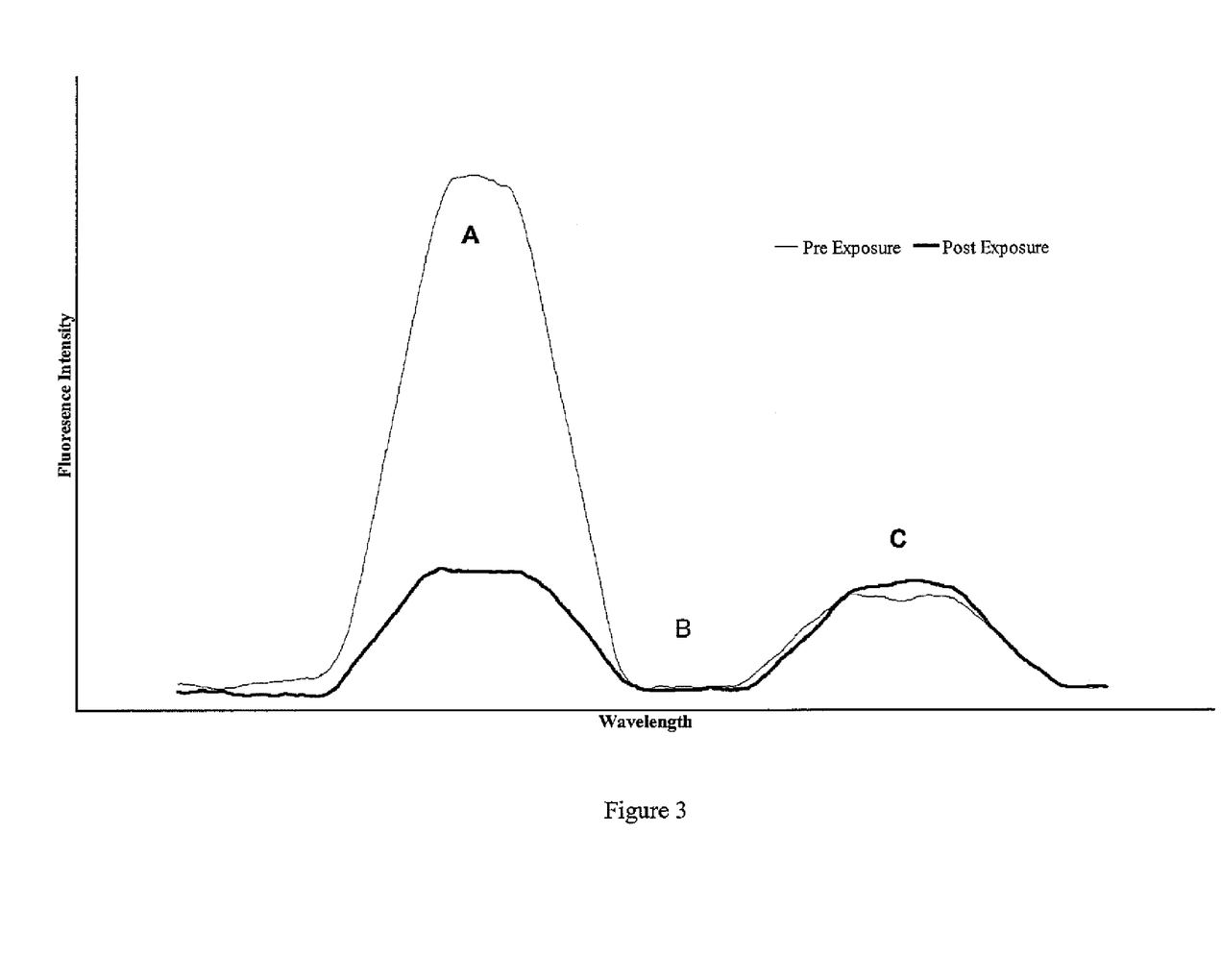
FIG. 3 is a graph depicting the display of fluorescence values before and after exposure of the sampling device to TNT.

Prior to deploying PSD 5 for detection of an analyte, the baseline or pre-exposure fluorescence values for each PSD 5 at the desired wavelengths must be determined. PSDR 28 is used to establish these pre-exposure values for each PSD 5. In FIGS. 2 and 3, baseline or pre-exposure scans are identified by dashed lines while post exposure scans are shown as solid lines.

To establish a pre-exposure scan or baseline reading, PSD 5 is placed in PSDR holder 44 and exposed to UV light by UV excitation source 40. The average fluorescence emission is measured at wavelengths selected for AFP 22 (area A), reference standard 28 (area C) and baseline fluorescence (area B) for each PSD 5. During excitation, filter wheel 56 automatically shifts first to the filter corresponding to the fluorescence wavelength of AFP 22 followed by rotations to the filter for baseline fluorescence and subsequently to the filter corresponding to the wavelength of fluorescence for reference standard 24. Thus, each filter is positioned between waveguide 10 and PMT 40 thereby permitting only UV light of the desired wavelength to pass to PMT 40 for analysis. One skilled in the art will recognize that the order of the selected filters is not critical to the current invention.

As shown in FIGS. 2 and 3, the resulting fluorescence value can be depicted as a graphical trace for each filter. Scan times are selected to ensure a sufficient period of time to generate a stable reading. Typically, scan times for AFP 22 (area A) and reference standard 28 (area C) range from about 3 to about 30 seconds with the preferred scan times being ten seconds. Scan times for the intervening baseline (area B) range from about 3 to about 30 seconds with a preferred scan time of about ten seconds.

In this method, the average baseline value (area B) is subtracted from the average PMT values for the AFP peak fluorescence (indicated as area A) and the reference standard peak fluorescence (indicated as area C). A ratio is generated by dividing the baselined reference standard 24 value by the baselined AFP 22 [(Reference Standard—Baseline)/(AFP—Baseline)]. This ratio is recorded and logged as the initial "Pre-exposure Ratio" for each PSD 5 prior to deployment in the field. Preferably, PSDR 28, or a suitably programmed computer, automatically records and stores the Pre-exposure ratio for each PSD 5 and associates this value with each PSD 5 using identification number 32.

Following placement in the field for the desired period of time, PSD 5 is collected and re-interrogated by PSDR 28. Typically when placed in the field, PSD 5 should be oriented such that AFP 22 is exposed to the surrounding environment. As noted above, the post-exposure scan in FIGS. 2 and 3 is depicted as a solid line. FIG. 2 depicts a blank or PSD 5 which was not exposed to a target analyte and FIG. 3 depicts the scan of a PSD 5 which was exposed to TNT. As depicted in FIG. 3, AFP 22 has been quenched by exposure to the TNT reducing the fluorescence peak A associated with AFP. In FIG. 3, the resulting R value is 5.232 and in FIG. 2, the resulting R value is 0.941. In general, R values between about 0.85 and about 1.1 indicate a negative test for the target analyte.

During post-exposure interrogation, fluorescence is measured at the same wavelengths used during establishment of the Pre-exposure Ratio. The resulting "Post-Exposure Ratio" is determined in the same manner as the Pre-exposure Ratio and then divided by the Pre-exposure Ratio. If the AFP has not been quenched by exposure to a target analyte, the fluorescence peak for AFP 22 will be virtually unchanged. As a result, the value obtained by dividing the Pre-exposure Ratio into the Post-exposure ratio will be approximately equal to one. If the AFP quenched, indicating the presence of nitroaromatic explosives, the value obtained by dividing the Pre-exposure Ratio into the Post-exposure ratio will be greater than one. The resulting ratio is known as the R value. Thus, the scans depicted in FIG. 2 would yield an R value of approximately 1 while the scans of FIG. 3 will yield an R value of greater than 1 thereby indicating a positive result.

In the preferred embodiment, PSDR 28 automatically generates the R value for each PSD 5. Automatic generation of R values is enabled by entering the identification number or code 32 of each exposed PSD 5. PSDR 28 associates code 32 with the pre-exposure fluorescence values and automatically performs the calculations discussed above to generate the R value. Thus, the only value required to be displayed on LCD readout 52 is the R value.

The current invention has been described predominately with reference to the preferred embodiment. However, other embodiments of the current invention will be apparent to those skilled in the art from a consideration of this specification and/or practice of the invention disclosed herein. Accordingly, the foregoing specification is considered merely exemplary of the current invention. The true scope of the current invention is defined by the following claims.

We claim:

1. A method for determining the presence of a target analyte comprising:
   providing a passive sampling device,
      said passive sampling device comprising a waveguide having first and second sides;
      an AFP compound carried by said first side of said waveguide, said AFP compound fluoresces when exposed to ultraviolet light, said fluorescence of said AFP compound is quenched by exposure of said AFP compound to a target analyte;
      a reference standard carried by said second side of said waveguide, said reference standard, when exposed to ultraviolet light, fluoresces at a wavelength distinct from the fluorescence of said AFP compound, and wherein fluorescence of said reference standard is not substantially quenched when said reference standard is exposed to said target analyte;
   providing a passive sampling device reader,
      said passive sampling device reader comprising a UV light source, at least three short-pass filters and a photomultiplier tube suitable for detecting fluorescent emissions;
   using said passive sampling device reader to determine a pre-exposure value for said passive sampling device prior to exposure of said passive sampling device to said target analyte by contacting said passive sampling device with UV light thereby generating a fluorescent emission from said AFP compound and from said reference standard measuring the pre-exposure fluorescent emissions for said AFP compound and said reference standard;

exposing said passive sampling device to said target analyte by placing said passive sampling device in an area to be tested for said target analyte for a period of time thereby exposing said passive sampling device to the surrounding environment;

collecting said passive sampling device and; and, using said passive sampling device reader to determine the capture and retention of said analyte by said AFP compound by contacting said passive sampling device with UV light thereby generating a post-exposure fluorescent emission from said AFP compound and from said reference standard and comparing said post-exposure fluorescent emissions to said pre-exposure fluorescent emissions for said passive sampling device.

2. A method for determining the presence of a target analyte comprising:

exciting an AFP compound and a reference standard with UV light thereby producing detectible fluorescent emission;

determining an initial average fluorescence emission of said AFP compound in response to UV light prior to contacting said AFP compound with a target analyte;

determining an initial average fluorescence emission of said reference standard in response to UV light;

determining a pre-exposure ratio by dividing the initial average fluorescence emission of an AFP compound into the initial average fluorescence emission of said reference standard;

exposing said AFP compound to said target analyte by placing said passive sampling device in an area to be tested for said target analyte for a period of time thereby exposing said passive sampling device to the surrounding environment;

following the step of exposing said AFP compound to a target analyte, collecting said passive sampling device and exciting an AFP compound and a reference standard with UV light thereby producing detectible fluorescent emission;

determining an average fluorescence emission of said AFP compound post-analyte exposure;

determining an average fluorescence emission of said reference standard post-analyte exposure;

determining a post-exposure ratio by dividing the post-exposure average fluorescence emission of an AFP compound into the post-exposure average fluorescence emission of said reference standard; and, dividing the pre-exposure ratio into the post-exposure ratio wherein a resulting value of greater than one indicates the presence of a target analyte.

3. The method of claim 2, further comprising the steps of:

determining a pre-exposure baseline fluorescence emission in response to said UV light, wherein the initial average fluorescence emission of said AFP compound is determined in relation to said baseline fluorescence emission and wherein the initial average fluorescence emission of said reference standard is determined in relation to said baseline fluorescence emission; and, determining a post-exposure baseline fluorescence emission in response to said UV light, wherein the post-exposure average fluorescence emission of said AFP compound is determined in relation to said baseline fluorescence emission and wherein the post-exposure average fluorescence emission of said reference standard is determined in relation to said baseline fluorescence emission.

4. The method of claim 2, wherein said steps of determining pre- and post-exposure baseline fluorescence emission in response to UV light determine said baseline fluorescence at a wavelength between about 500 nm and about 580 nm by passing said fluorescent emission through a filter.

5. The method of claim 2, wherein said UV light has a wavelength between about 365 nm and 410 nm and further comprising the step of passing said light through a 410 nm short pass filter prior to contacting said AFP compound and said reference standard.

6. The method of claim 5, wherein said steps of determining an initial average fluorescence emission of said AFP compound in response to UV light prior to target analyte exposure and post-exposure further comprise passing said fluorescent emission through a filter.

7. The method of claim 6, wherein said filter isolates a wavelength of light between about 450 nm and about 480 nm.

8. The method of claim 4, wherein said steps of determining an initial average fluorescence emission of said reference standard in response to UV light prior to target analyte exposure and post-exposure further comprise passing said fluorescent emission through a filter.

9. The method of claim 8, wherein said filter isolates a wavelength of light of at least about 580 nm.

10. A method for determining the presence of a target analyte comprising:

providing a passive sampling device carrying an AFP compound and a reference standard, said AFP compound and said reference standard produce a detectible fluorescent emission when excited by UV light;

determining a pre-exposure baseline fluorescence emission in response to said UV light for said passive sampling device;

exciting said AFP compound and a reference standard with UV light thereby producing detectible fluorescent emission;

determining an initial average fluorescence emission of said AFP compound in response to UV light prior to contacting said AFP compound with a target analyte, wherein said initial average fluorescent emission is determined in relation to said pre-exposure baseline fluorescence emission;

determining an initial average fluorescence emission of said reference standard in response to UV light wherein said initial average fluorescent emission is determined in relation to said pre-exposure baseline fluorescence emission;

determining a pre-exposure ratio by dividing the initial average fluorescence emission of said AFP compound into the initial average fluorescence emission of said reference standard;

exposing said AFP compound to said target analyte by placing said passive sampling device in an area to be tested for said target analyte for a period of time thereby exposing said passive sampling device to the surrounding environment;

following the step of exposing said AFP compound to a target analyte collecting said passive sampling device and determining a post-exposure baseline fluorescence emission in response to said UV light for said passive sampling device;

determining an average fluorescence emission in response to said UV light of said AFP compound post-analyte exposure wherein said post-exposure average fluorescent emission is determined in relation to said pre-exposure baseline fluorescence emission;

determining an average fluorescence emission in response to said UV light of said reference standard post-analyte exposure wherein said post-exposure average fluorescent emission is determined in relation to said pre-exposure baseline fluorescence emission;

determining a post-exposure ratio by dividing the post-exposure average fluorescence emission of an AFP compound into the post-exposure average fluorescence emission of said reference standard; and, dividing the pre-exposure ratio into the post-exposure ratio wherein a resulting value of greater than one indicates the presence of a target analyte.

11. The method of claim 10, wherein said steps of determining pre- and post-exposure baseline fluorescence emission in response to UV light determine said baseline fluorescence at a wavelength between about 500 nm and about 580 nm by passing said fluorescent emission through a filter.

12. The method of claim 10, wherein said steps of determining pre- and post-exposure baseline fluorescence emission in response to UV light determine said baseline fluorescence at a wavelength between about 500 nm and about 580 nm by passing said fluorescent emission through a filter and wherein said UV light has a wavelength between about 365 nm and 410 nm and further comprising the step of passing said light through a 410 nm short pass filter prior to contacting said AFP compound and said reference standard.

13. The method of claim 12, wherein said steps of determining an initial average fluorescence emission of said AFP compound in response to UV light prior to target analyte exposure and post-exposure further comprise passing said fluorescent emission through a filter.

14. The method of claim 13, wherein said filter isolates a wavelength of light between about 450 nm and about 480 nm.

15. The method of claim 14, wherein said steps of determining an initial average fluorescence emission of said reference standard in response to UV light prior to target analyte exposure and post-exposure further comprise passing said fluorescent emission through a filter.

16. The method of claim 15, wherein said filter isolates a wavelength of light of at least about 580 nm.

\* \* \* \* \*